(12) United States Patent
Kockler

(10) Patent No.: US 10,118,875 B1
(45) Date of Patent: Nov. 6, 2018

(54) ENERGY EFFICIENT METHODS FOR ISOMERIZATION OF A C5-C6 FRACTION WITH DIVIDING WALL FRACTIONAL DISTILLATION

(71) Applicant: David Norbert Kockler, Arlington Heights, IL (US)

(72) Inventor: David Norbert Kockler, Arlington Heights, IL (US)

( * ) Notice: Subject to any disclaimer, the term of this patent is extended or adjusted under 35 U.S.C. 154(b) by 0 days.

(21) Appl. No.: 15/703,304

(22) Filed: Sep. 13, 2017

(51) Int. Cl.
  *C07C 5/27* (2006.01)
  *C07C 7/04* (2006.01)
  *B01D 3/00* (2006.01)
  *B01D 3/14* (2006.01)

(52) U.S. Cl.
  CPC .............. *C07C 5/277* (2013.01); *B01D 3/009* (2013.01); *B01D 3/141* (2013.01)

(58) Field of Classification Search
  None
  See application file for complete search history.

(56) References Cited

U.S. PATENT DOCUMENTS

| | | | | |
|---|---|---|---|---|
| 6,395,950 B1* | 5/2002 | Rice | ........................ | B01D 3/141 585/734 |
| 6,540,907 B1* | 4/2003 | Towler | .................... | B01D 3/141 208/211 |
| 6,552,242 B1* | 4/2003 | Rice | ........................ | B01D 3/141 208/347 |
| 6,927,314 B1* | 8/2005 | Schultz | .................. | B01D 3/141 585/734 |
| 7,429,685 B2* | 9/2008 | Bouchy | .................. | C10G 65/14 585/301 |
| 2015/0251972 A1* | 9/2015 | Shecterle | ............... | C10G 35/00 585/302 |
| 2016/0311732 A1* | 10/2016 | Banerjee | ................ | C10G 65/08 |

* cited by examiner

*Primary Examiner* — Philip Y Louie

(57) ABSTRACT

This invention relates to a method of separating an isomerization zone effluent mixture comprising between 5 and 7 carbon atoms into high octane isomerate product streams and low octane streams which may be recycled to the isomerization zone. The separation process makes use of a dividing wall column to efficiently perform the separation of isopentane and high octane multibranched paraffins from low octane straight chain and single branched paraffins.

13 Claims, 2 Drawing Sheets

ENERGY EFFICIENT METHODS FOR ISOMERIZATION OF A C5-C6 FRACTION WITH DIVIDING WALL FRACTIONAL DISTILLATION

BACKGROUND OF THE INVENTION

This invention relates generally to the isomerization of hydrocarbons. More specifically, the invention involves an isomerization zone and an isomerized product fractionation zone in which a stabilized effluent stream from the isomerization zone is separated into high octane product streams and low octane product streams by means of fractional distillation and by making use of a dividing wall column and a non-divided column. The stabilized isomerization zone effluent is generally comprised of hydrocarbons containing between 5 and 7 carbon atoms per molecule.

Isomerization is an important process used in the petroleum industry to increase the research octane number (RON) of light naphtha feeds. In current practice, the naphtha (C5-C10 fraction) obtained from atmospheric distillation of petroleum is separated by means of fractional distillation into light naphtha and heavy naphtha. The light naphtha is generally sent to an isomerization process unit and the heavy naphtha is generally sent to a catalytic reforming process unit. In both the isomerization process unit and the catalytic reforming process unit, the RON values of the respective naphtha fractions are improved. High RON values are a desired characteristic for naphtha streams that are sent to the gasoline pool because gasoline spark ignition engines perform better and can achieve greater fuel efficiency with higher RON gasoline.

The product streams from isomerization processes (isomerate), unlike the product streams from catalytic reforming processes (reformate) are virtually free of aromatic compounds. Low aromatic concentrations are a desired characteristic for naphtha streams that are sent to the gasoline pool because of increasingly stringent specifications for aromatics in gasoline. As a result of the increasingly stringent specifications for aromatics in gasoline, there has been growing interest in the petroleum industry in processing light naphtha in isomerization process units.

The present invention relates in particular to C5-C6 fraction light naphtha feeds to isomerization units that are rich in C5-C7 molecules. The C5-C6 fraction is generally produced through fractionation of full range naphtha in such a manner that the majority of the C7 molecules found in the full range naphtha are excluded from the C5-C6 fraction. The major portion of C7 molecules found in full range naphtha are excluded from the C5-C6 fraction that is fed to most light naphtha isomerization units because excessive cracking of C7 molecules takes place at typical isomerization reactor conditions suitable for isomerizing C5-C6 rich feeds. However, a small percentage of the C7 molecules from the full range naphtha will be included in the C5-C6 fraction as a result of overlap that is characteristic of distillation processes. Therefore, the term "C5-C6 fraction" will be used herein to designate a fraction that contains C5-C7 molecules but in practice is materially a C5-C6 fraction.

Once-through isomerization processes, or processes in which the isomerization reactor effluent is not separated into high octane and low octane streams for the purpose of recycling low octane streams to the isomerization reactor, are typically limited to a maximum isomerate product RON of about 84 with typical isomerization unit feeds. The terms "isomerization unit feed" and "light naphtha feed" are used interchangeably herein to refer to the feed stream that is supplied to the isomerization unit for processing into isomerate product. Once-through isomerization processes generally cannot achieve isomerate product RON values in excess of 84 because the isomerization reactor conversion cannot exceed the equilibrium conversion attainable with commercial isomerization catalysts under isomerization conditions.

Consequently, the separation of the isomerization reactor effluent in isomerization processes is critical to achieving desired RON targets for isomerate product that exceed a RON of 84. In order to maximize the isomerate product RON, it is desirable to separate the isomerization reactor effluent into different molecular structural classes. In general, multibranched paraffins (paraffins having two or more branches) have higher RON values than straight chain and single branched compounds. It is desirable, therefore, to separate the high octane multibranched compounds (as well as high octane isopentane) as isomerate product and recycle lower octane straight chain and single branched paraffins to the reactor feed. It is generally not desirable to recycle multibranched paraffins to the reactor feed because doing so would result in the conversion of a portion of the high octane multibranched paraffins into lower octane straight chain and single branched paraffins in the isomerization reactor.

Several methods that have been utilized to achieve the desired separation between high octane components and low octane components in isomerization reactor effluents in applications with C5-C6 fraction light naphtha feeds are described in Domergue, B., and Watripont, L. *World Refining*, May 2000, p. 26-30 and in Aranovich, I., Reis, E., and Shakun, A. Hydrocarbon Engineering, April 2012, p. 20-26. Each of the separation methods discussed in these two articles improves the isomerate product RON compared with the isomerate product RON that can be obtained in a once-through isomerization process.

The separation methods discussed in the Domergue and Watripont and the Aranovich, Reis, and Shakun articles that can be used to increase the isomerate product RON include: the use of a Deisopentanizer column to recover isopentane from the isomerization unit feed before the isomerization unit feed is introduced to the isomerization reactor; the use of a Deisohexanizer column to separate high octane and low octane C6 compounds from the isomerization reactor effluent; the use of a Deisopentanizer column in conjunction with a molecular sieve adsorption process; the use of a Deisohexanizer column in conjunction with a molecular sieve adsorption process; and the use of a the use of a Deisopentanizer column in conjunction with a Depentanizer column and a Deisohexanizer column.

In each configuration discussed in the Domergue and Watripont and the Aranovich, Reis, and Shakun articles, the placement of the Deisopentanizer is upstream of the isomerization zone and the placement of the Depentanizer column and the Deisohexanizer column is downstream of the isomerization zone.

The majority of the configurations discussed in the Domergue and Watripont and the Aranovich, Reis, and Shakun articles rely on separation and recycle of low octane streams to the isomerization reactor as a means to increase the isomerate product RON. A Deisohexanizer, for example, separates high octane C6 molecules (principally dimethylbutanes) from low octane C6 molecules (principally normal hexane and methylpentanes). The resulting high octane stream that is produced by the Deisohexanizer column separation is withdrawn from the isomerization process as a product stream and the low octane stream that is produced by the Deisohexanizer column separation is recycled to the isomerization reactor. A composite isomerate product RON value of approximately 88 can be achieved through the use of a configuration with solely a Deisohexanizer in the product fractionation zone.

In order to achieve composite isomerate product RON values in the range of 88 to 93, it is necessary to include low octane C5 molecules in the recycle to the isomerization reactor along with low octane C6 molecules. Since the separation and recycle of low octane C5 and C6 molecules cannot be accomplished with only a Deisohexanizer column, a more complex process scheme is required to achieve composite isomerate product RON values in the range of 88 to 93. The separation of high octane and low octane C5 and C6 molecules has traditionally been accomplished through configurations which rely on pairing distillation with a molecular adsorption process or alternately by using a complex distillation configuration in which a Deisopentanizer column is placed upstream of the isomerization reactor in a feed fractionation zone and a Depentanizer column and a Deisohexanizer column are used in an isomerized product fractionation zone downstream of the isomerization reactors. In the latter configuration, the isomerization reactor effluent is sent to a Depentanizer column in an isomerized product fractionation zone, where the Depentanizer is used to separate a C5 rich stream from the balance of the isomerization reactor effluent. A C5 rich stream is removed from the first end of the Depentanizer column and sent to a Deisopentanizer column in the feed fractionation zone, where high octane isopentane is separated from the normal pentane in the C5 rich stream (the Deisopentanizer receives a combined feed consisting of the isomerization unit feed and the C5 rich stream that is recycled from the Depentanizer column and the Deisopentanizer separates isopentane from the balance of the combined feed). Isopentane from the C5 rich stream is removed from the first end of the Deisopentanizer column as a high octane isomerate product and normal pentane from the C5 rich stream is removed from the second end of the Deisopentanizer column and recycled to the isomerization reactor. The balance of the isomerization reactor effluent which is fed to the Depentanizer (in the isomerized product fractionation zone) is removed from the second end of the Depentanizer and sent to a Deisohexanizer column to separate high octane and low octane C6 compounds. The term "first end of the column" is used herein to refer to the overhead distillate system (at the top) of the column and the term "second end of the column" is used herein to refer to the bottom of the column.

Achieving composite isomerate product RON values in the range of 88 to 93 using currently known art requires high energy inputs to separate high octane streams for removal from the isomerization process as isomerate products and low octane streams for recycling to the isomerization reactor. The most energy intensive separations are the distillation processes which separate close boiling molecules; in particular the separation of dimethyl butane from methylpentane in a Deisohexanizer and the separation of isopentane from normal pentane in a Deisopentanizer require large energy inputs to the respective distillation column reboilers to perform the desired separations.

High energy inputs may also be required in isomerization configurations which depend exclusively on a Deisohexanizer for separating high octane streams from low octane streams. High energy usage is generally required when a configuration with only a Deisohexanizer is used to separate high and low octane streams to produce composite isomerate products with RON values in the range of about 86 to 88.

None of the methods outlined in the Domergue and Watripont article or the Aranovich, Reis, and Shakun article make use of a dividing wall column to separate high octane components and low octane components in isomerization reactor effluents. In general, a significant improvement in the efficiency of separation can be achieved through separations that are performed in dividing wall columns compared with the use of multiple non-divided columns to perform the same separations because of the superior thermal efficiency of dividing wall columns.

One novel process scheme for separating high octane components and low octane components in isomerization reactor effluents in applications with C5-C6 fraction light naphtha feeds is described in U.S. Pat. No. 6,395,951. The separation scheme presented in U.S. Pat. No. 6,395,951 employs a unique configuration consisting of an adsorptive separation zone followed by a dividing wall fractionation zone to separate isomerization zone effluent streams into high octane and low octane fractions. Low octane straight chain paraffins such as normal pentane and normal hexane are removed in the absorptive separation zone for recycle to the isomerization zone and a dividing wall column in the dividing wall fractionation zone separates low octane single branched C6 paraffins from high octane multibranched C6 paraffins and from a high octane C6-C7 bottoms stream. The separation in the dividing wall column for this design is notably different than separations which are made in typical deisohexanizer column designs in that the majority of (high octane) methylcyclopentane is intentionally removed as part of the high octane C6-C7 bottoms stream. This contrasts with a typical deisohexanizer design that does not have an adsorptive separation section to remove low octane straight chain paraffins. Normal hexane (a straight chain molecule) is present in the feed to a typical deisohexanizer column that does not have an adsorptive separation section to remove low octane straight chain paraffins, and because normal hexane has a very low octane value, it is desirable to include as much normal hexane as possible in the low octane fraction containing low octane paraffins with a single branch so that the normal hexane can be recycled to the isomerization zone for conversion to isomerized products. Normal hexane and methylcyclohexane are close boiling molecules, and as a result of including the majority of normal hexane in the low octane fraction containing low octane C6 paraffins with a single branch, the majority of methylcyclopentane is also removed from a typical deisohexanizer column in the low octane stream containing normal hexane and C6 paraffins with a single branch. In effect, the methods described in U.S. Pat. No. 6,395,951 use a dividing wall column to create high octane and low octane fractions that have different compositions with respect to methylcyclopentane than typical deisohexanizer separations.

The process scheme described in U.S. Pat. No. 6,395,951, like the other process schemes discussed in the Domergue and Watripont and Aranovich, Reis, and Shakun articles for producing composite isomerate products with RON values in the range of 88 to 93, requires a large capital investment to construct, has high utility requirements, and is difficult to operate. A process scheme which reduces the utility costs, capital costs, and operating complexity of separating isomerization reactor effluent streams to produce a composite isomerate product with a RON value in the range of 88 to 93 would constitute an improvement over the current art.

The use of a fractional distillation scheme involving a dividing wall column and a non-divided column in the present invention to separate an isomerization reactor effluent in a process with a C5-C6 fraction light naphtha feed provides significant advantages versus methods that are currently publically known because the dividing wall fractional distillation process is more energy efficient, less costly to construct, and easier to operate than currently known processes. Unlike currently known methods for producing composite isomerate products with RON values in the range of 88 to 93, the present invention does not require the use of an adsorptive separation zone or a plurality of fractionation zones in which energy intensive separations are performed in each fractionation zone.

BRIEF SUMMARY OF THE INVENTION

The overall isomerization process for processing a C5-C6 light naphtha feed can be generally described as divided into two zones: an isomerization zone; and an isomerized product fractionation zone where the reactor effluent is stabilized and the stabilizer bottoms is separated into high octane isomerized product streams and low octane recycle streams. Some isomerization processes also incorporate the use of a feed fractionation zone for the purpose of recovering isopentane as an isomerate product stream. In isomerization units configured with a feed fractionation zone, the isomerization unit feed is sent to a Deisopentanizer column, where the isopentane rich isomerate product is removed from the first end of the column and the balance of the isomerization unit feed is removed from the second end of the column and sent to the downstream isomerization zone. The invention provides an improvement to the processes in the isomerized product fractionation zone and eliminates the need for a Deisopentanizer in a feed fractionation zone.

The energy savings that can be obtained through the use of this invention relies upon the use of a dividing wall column to simultaneously perform two energy intensive separations, namely the separation of isopentane from normal pentane and higher boiling molecules and the separation of paraffins containing 6 carbon atoms with at least two branches from normal hexane and paraffins containing 6 carbon atoms and a single branch. In the current art, these separations take place in two separate distillation columns (Deisopentanizer and Deisohexanizer) and take place in two distinct fractionation zones (feed fractionation zone and isomerized product fractionation zone) in the isomerization process. The present invention differs from the current art in that it incorporates a distillation process which includes the functions of a Deisopentanizer column, a Depentanizer column, and a Deisohexanizer column, but in a configuration in which all of the distillation columns are placed downstream of the isomerization zone. Energy savings are achieved through the use of a dividing wall column to simultaneously perform two energy intensive separations because a single (reboiler) energy input to the dividing wall column is used in an efficient manner to perform the two separations in the isomerization process that require the greatest amount of energy.

One purpose of the invention is to separate the reactor effluent from isomerization reactors into high octane streams and low octane streams for the purpose of producing a high octane isomerate product and recycling the low octane streams to the isomerization reactors. The isomerization reactor effluent stream is generally passed to a stabilizer column which provides a stabilized isomerized product stream that is removed from the bottom of the stabilizer column. The process which is used to perform the separation of the stabilized isomerized product may create one or more intermediate streams. The term "intermediate stream" is used herein to describe a stream that has not yet been fully separated into high octane and low octane fractions and requires further separation to divide the stream into high octane and low octane fractions. The invention will separate the stabilized isomerized product stream comprising C5-C7 paraffins with varying degrees of branching into high octane fraction A comprising the major portion of isopentane, low octane fraction B comprising the major portion of normal pentane, high octane fraction C comprising the major portion of paraffins containing 6 carbon atoms with at least two branches, low octane fraction D comprising the major portion of normal hexane and paraffins containing 6 carbon atoms and a single branch, and high octane fraction E comprising the major portion of hydrocarbons containing at least 7 carbon atoms. The term "major portion of" is used herein to refer to the major portion of referenced molecules which are present in all of the feed streams that are sent to the dividing wall column in the isomerized product fractionation zone. For example, if a single column feed consisting of a stabilized isomerized product stream is fed to the dividing wall column in the isomerized product fractionation zone contains 99 isopentane molecules, then Fraction A will contain at least 50 isopentane molecules.

The stabilized isomerized product mixture is separated in a process that includes a dividing wall column and a non-divided column. The mixture is introduced into a dividing wall column which is divided into first and second parallel fractionation zones by a dividing wall that extends from a lower end to an upper end within the column, with the first and second parallel fractionation zones being in open communication at the upper ends of each fractionation zone with an upper section of the column that is undivided and with the first and second parallel fractionation zones being in open communication at the lower ends of each fractionation zone with a lower section of the column that is undivided. The first parallel fractionation zone is defined as the parallel fractionation zone on the feed side of the dividing wall (the parallel fractionation zone on the side of the dividing wall which faces the stabilized isomerized product feed entry point into the column) and the second parallel fractionation zone is defined as the parallel fractionation zone on the side of the dividing wall which faces away from the first parallel fractionation zone.

The stabilized isomerized product mixture is introduced to the dividing wall column at an intermediate point of the first fractionation zone. An intermediate stream comprising the major portion of normal pentane and paraffins containing 6 carbon atoms with at least two branches is removed from an intermediate point of the second fractionation zone of the dividing wall column. The intermediate stream comprising the major portion of normal pentane and paraffins containing 6 carbon atoms with at least two branches is passed to a non-divided second column. A high octane stream comprising the major portion of isopentane is removed from the first end of the dividing wall column and a second high octane stream comprising the major portion of hydrocarbons containing at least 7 carbon atoms is removed from the second end of the dividing wall column. A low octane stream comprising the major portion of normal hexane and paraffins containing 6 carbon atoms and a single branch is removed as a side stream from an intermediate point in the lower undivided section of the dividing wall column. A low octane stream comprising the major portion of normal pentane is removed from the first end of the non-divided column and a high octane stream comprising the major portion of hydrocarbons containing 6 carbon atoms with at least two branches is removed from the second end of the non-divided column.

DETAILED DESCRIPTION OF THE INVENTION

Figure 1:
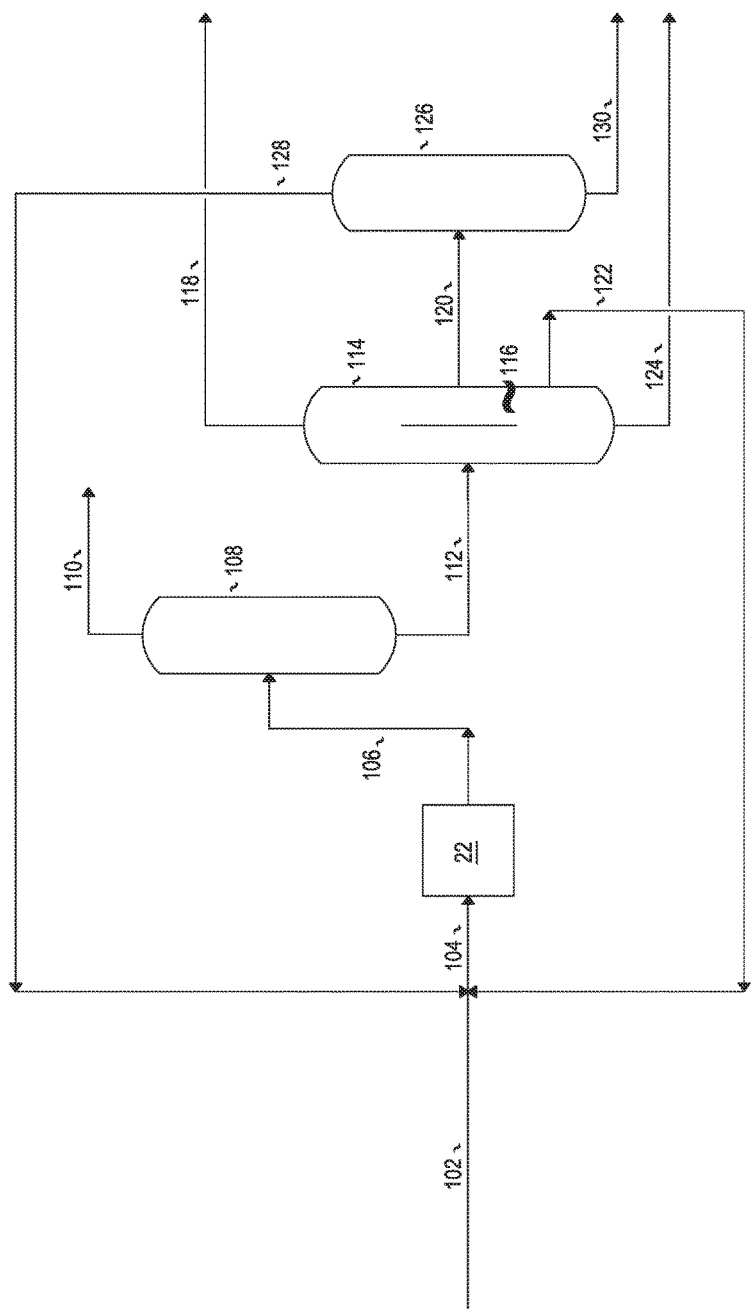
FIG. 1 provides a simplified process flow diagram of a first preferred embodiment of the invention.

The detailed description is provided herein is exemplary and provides examples of preferred embodiments of the invention. The description of the exemplary embodiments is not intended to limit the use of the invention to only the exemplary embodiments of the invention described herein.

The invention is not restricted to any particular type of isomerization process; however, the invention is well suited for isomerization processes which are designed to process a light naphtha feed comprised of a C5-C6 fraction. The invention is also well suited for applications in which recycle of low octane isomerized products is required to meet the RON specification for the isomerate product from the overall isomerization process. The term "overall isomerization process" is used herein to refer to the entirety of the isomerization process. The invention is well suited for isomerization applications with composite isomerate product RON targets in the range of about 86 to 88 and is especially well suited for isomerization applications with composite isomerate product RON targets in the range of about 88 to 93.

The isomerization zone may be any form of isomerization zone which processes one or more isomerization unit feed streams containing C5-C6 straight chain hydrocarbons and branched chain hydrocarbons and converts the straight chain hydrocarbons into branched chain hydrocarbons and converts branched chain paraffins into paraffins with an increased degree of branching. A suitable feedstock for use with the invention will contain significant amounts of C5 and C6 molecules. The isomerization unit feed should contain at least normal pentane and normal hexane. The preferred isomerization unit feed will be rich in molecules which have five to six carbon atoms, meaning that at least 50% of the molecules in the isomerization unit feed will be C5 or C6 molecules.

Isomerization processes which favor the isomerization of C5-C6 fraction isomerization unit feeds are known to cause significant amounts of cracking of molecules in the feed which contain at least seven carbon atoms. Cracking of molecules in the isomerization unit feed which contain at least seven carbon atoms results in the production of light hydrocarbons which generally have a lower economic value than molecules which contain at least seven carbon atoms. Excessive cracking of molecules which contain at least seven carbon atoms will also result in excessive consumption of hydrogen in the isomerization process. Consequently, it is preferred to limit the concentration of molecules in the isomerization unit feed which contain at least seven carbon atoms to a maximum of 5 wt %.

The ratio of C5/C6 in the isomerization unit feed is an important consideration because the present invention separates the stabilized isomerized product into high octane and low octane streams through the use of a dividing wall column. Dividing wall columns operate most efficiently when the top section column product(s), middle section column product(s), and bottom section column product(s) are nearly equivalent in molar flowrate. For efficient separation of products in the dividing wall column used in the invention, it is preferred that the isomerization unit feed have a minimum C5/C6 molar ratio of 1:5; more preferably the isomerization unit feed will have a minimum C5/C6 molar ratio of 1:3; and most preferably the isomerization unit feed will have a minimum C5/C6 molar ratio of 2:3.

The typical design features of isomerization zones which process C5-C6 fraction light naphtha feeds are well known to experienced practitioners of the art and only a general summary of these features are discussed herein. The term "combined isomerization zone feed" is used herein to refer to the composite stream consisting of the isomerization unit feed combined together with all of the streams which are recycled back to the isomerization zone. The isomerization zone includes all of the equipment and processes necessary to efficiently isomerize the combined isomerization zone feed.

Various types of isomerization catalysts may be used in the isomerization process that is associated with this invention, including catalysts which can be lumped into classifications which are generally called chlorinated alumina catalysts, zeolite catalysts, and sulfated zirconium metal oxide catalysts. Each category of catalysts has a different preferred range of isomerization reactor operating conditions (such as operating temperature, operating pressure, and molar hydrogen/hydrocarbon ratio). A brief summary of the preferred ranges of isomerization reactor operating conditions for each of the aforementioned categories of catalysts can be found in the Aranovich, Reis, and Shakun article.

Hydrogen gas is generally mixed with the combined isomerization zone feed in order to provide hydrogen to meet the stoichiometric requirement of side reactions which take place during isomerization. It is a common practice to use a molar hydrogen/hydrocarbon ratio at the isomerization reactor inlet that provides hydrogen in excess of the stoichiometric requirement of the side reactions. The use of hydrogen gas in amounts in excess of the stoichiometric requirement of the side reactions improves isomerization catalyst life by suppressing side reactions which deposit coke on the catalyst surface.

A two stage isomerization reactor system consisting of two reactors in series is commonly used in isomerization zones, but a two stage reactor system is not a necessary feature of the isomerization zone associated with the present invention. A two stage reactor system with specialized valving permits the replacement of catalyst in one of the two reactors to take place while the second reactor remains online. This provides the advantage that the isomerization unit with a two reactor system does not need to be taken off stream during replacement of catalyst in one of the two reactors; in contrast an isomerization unit with a single reactor system must be taken off line during catalyst replacements.

A first exemplary embodiment of the invention is shown in FIG. 1. This drawing is a simplified process flow diagram which does not show details for the process system such as instrumentation and controls, valves, pumps, reboilers, condensers, and heat exchangers. Such details are known to experienced practitioners of the art.

The isomerization unit feed is sent via line 102 to isomerization zone 22. Two recycle streams from the isomerized product fractionation zone are also sent to the isomerization zone. A normal pentane rich recycle stream is conducted via line 128 to line 102 and a C6 rich recycle stream is conducted via line 122 to line 102. The isomerization unit feed is mixed together with the normal pentane rich recycle stream and the C6 rich recycle stream and the three combined streams (the combined isomerization zone feed) are conducted via line 104 to isomerization zone 22.

Isomerization zone 22 shown in FIG. 1 illustrates the isomerization equipment and processes used to efficiently isomerize the combined isomerization zone feed which is conducted via line 104 to the isomerization zone. The combined isomerization zone feed is isomerized in isomerization zone 22 in the presence of isomerization catalysts and hydrogen. Isomerization may take place in one or more isomerization reactors in series arrangement.

The effluent stream from the isomerization reactors which is removed from isomerization zone 22 is sent to stabilizer 108 via line 106 to remove butane and light gases. A stabilized isomerized product is removed from the second end of stabilizer 108 and sent to a fractionation system consisting of dividing wall column 114 and non-divided column 126 to separate high octane streams from low octane streams. Butane and light gases are removed from the first end of stabilizer 108 via line 110. The stabilized isomerized product is sent to dividing wall column 114 via line 112. The dividing wall column contains two parallel fractionation zones which are divided by a vertical dividing wall 116. Dividing wall 116 is imperforate and therefore prevents flow of vapor or liquid from one parallel fractionation zone across the dividing wall to the other parallel fractionation zone. Above the top of each of the two parallel fractionation zones is an upper undivided fractionation zone and below the bottom of each of the two parallel fractionation zones is a lower undivided fractionation zone. Each of the two parallel fractionation zones are in open communication at the top of the parallel fractionation zones with the upper undivided fractionation zone and each of the two parallel fractionation zones are in open communication at the bottom of the parallel fractionation zones with the lower undivided fractionation zone. This arrangement restricts the flow of vapor and liquid from crossing from one parallel fractionation zone to another through dividing wall 116 but allows vapor and liquid to flow around the dividing wall from one parallel fractionation zone to another.

To simplify the discussion of the separation which takes place in dividing wall column 114, the separation will be discussed in terms of the following five fractions which are produced from the isomerized product fractionation zone: Fraction A comprising the major portion of isopentane, which represents the fraction with the lowest boiling point, Fraction B comprising the major portion of normal pentane, which represents the fraction with the second lowest boiling point, Fraction C comprising the major portion of paraffins containing 6 carbon atoms with at least two branches, which represents the fraction with the third lowest boiling point, Fraction D comprising the major portion of normal hexane and paraffins containing 6 carbon atoms and a single branch, which represents the fraction with the fourth lowest boiling point, and Fraction E comprising the major portion of hydrocarbons containing at least 7 carbon atoms which represents the fraction with the highest boiling point.

Fractions A, C, and E are rich in high octane components which makes it advantageous to use these fractions as constituents of the isomerate product that is produced in the overall isomerization process. Fractions B and D are rich in low octane components which can be further isomerized to produce high octane components. Therefore it would be more advantageous to recycle Fractions B and D to isomerization zone 22 rather than to use these fractions as constituents of the isomerate product that is produced in the overall isomerization process. Recycling Fractions B and D to the isomerization zone increases the octane of the composite isomerate product from the overall isomerization process.

The stabilized isomerized product is introduced at an intermediate point to the feed side, or first parallel fractionation zone of dividing wall column 114. The entirety of Fraction A as well as a portion of Fractions B and C are driven upwards in the first parallel fractionation zone and enter the upper undivided section of the column. In the upper undivided section of the column, Fraction A is driven upwards to the top of the column and the portions of Fractions B and C which were driven upwards in the first parallel fractionation zone drain down into the second parallel fractionation zone. Fraction A is removed via line 118 from the first end of the column as a high octane isomerate product stream.

The entirety of Fractions D and E as well as a portion of Fractions B and C drain down through the first parallel fractionation zone and enter the lower undivided section of the column. The portions of Fractions B and C which drained down through the first parallel fractionation zone are driven upward into the second parallel fractionation zone.

Within the second parallel fractionation zone, the portions of Fractions B and C which were driven upwards in the first parallel fractionation zone and drained down into the second parallel fractionation zone combine with the portions of Fractions B and C which drained down through the first parallel fractionation zone and were driven upward into the second parallel fractionation zone. The entirety of Fractions B and C are removed from an intermediate point in the second parallel fractionation zone via line 120 as a first side draw from the column.

In the lower undivided section of the column, Fraction E drains down to the bottom of the column and Fraction D drains down to an intermediate point in the lower undivided section of the column. Fraction E is removed via line 124 from the second end of the column as a high octane isomerate product stream. Fraction D is removed via line 122 from an intermediate point in the lower undivided section of the column as a second side draw from the column and returned to the isomerization zone.

The mixture containing Fractions B and C that is removed from an intermediate point of the second parallel fractionation zone of dividing wall column 114 is sent via line 120 to an intermediate point in non-divided column 126, where Fraction B is separated from Fraction C. Fraction B is removed from the first end of non-divided column 126 and returned via line 128 to isomerization zone 22. Fraction C is removed from the second end of non-divided column 126 via line 130 as a high octane isomerate product stream.

The composite high octane isomerate product from the overall isomerization process in the first exemplary embodiment is comprised from the sum of Fractions A, C, and E. Each of these three fractions are removed from the isomerized product fractionation zone and combined to form the composite isomerate product from the overall isomerization process.

In the first exemplary embodiment of the invention shown in FIG. 1, four streams are removed from dividing wall column 114. In this embodiment, Fractions D and E are separated in the lower undivided section of dividing wall column 114. It is also possible, however, to perform the separation of Fractions D and E in a second non-divided column by removing only three streams rather than four from dividing wall column 114. In a scenario where Fractions D and E are separated in a second non-divided column, the entirety of Fractions D and E drain down to the bottom of the dividing wall column. The stream removed from the second end of the dividing wall column containing a mixture of Fractions D and E would be sent to a second non-divided column, to separate Fractions D and E.

A second embodiment of the invention may be used in certain applications which do not require a sharp separation between Fraction B (containing the major portion of normal pentane) and Fraction C (containing the major portion of paraffins containing 6 carbon atoms with at least two branches), such as some applications with a composite isomerate product RON target less than about 90. In these applications, it may be possible to perform the separation of the stabilized isomerized product stream using only a dividing wall column. The advantage afforded by performing the separation of the stabilized isomerized product stream using only a dividing wall column is that capital costs for the isomerization unit are reduced by eliminating the need for a non-divided column to perform the separation between Fractions B and C.

Figure 2:
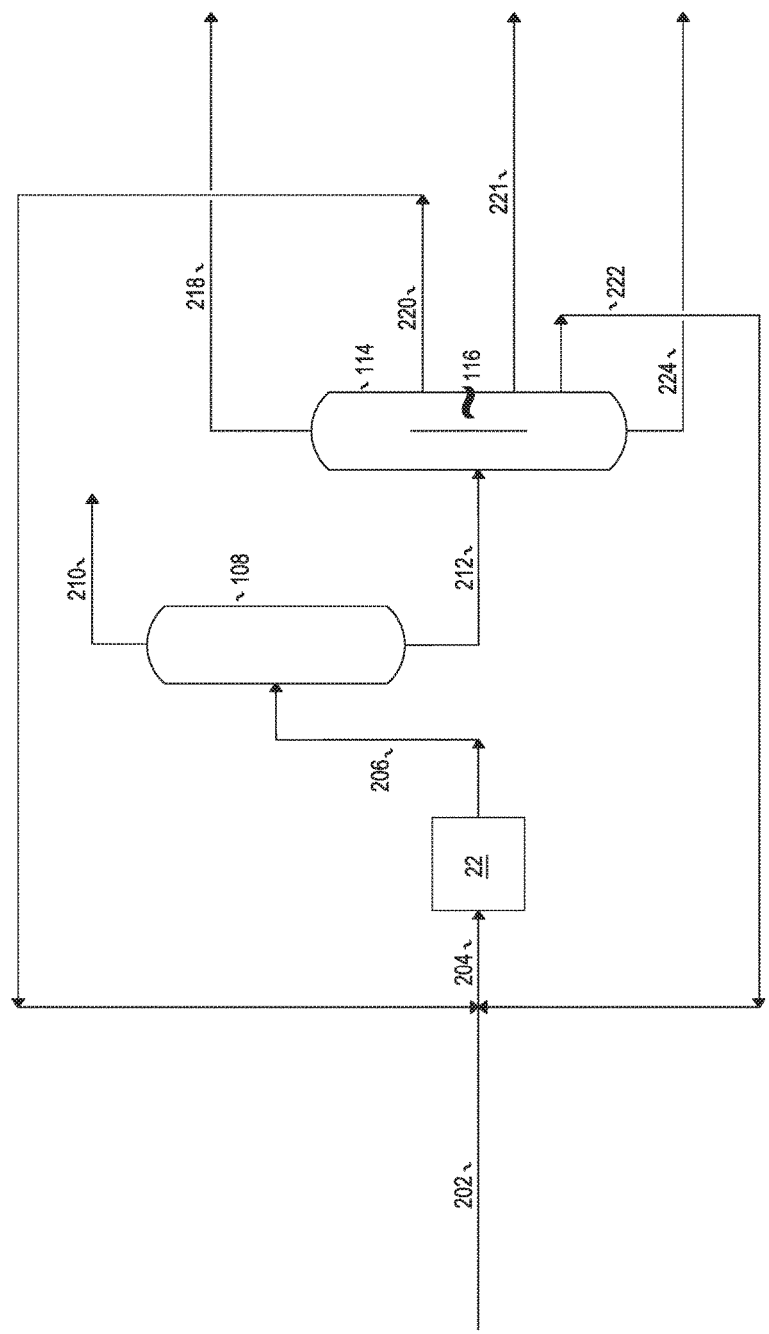
FIG. 2 provides a simplified process flow diagram of a second preferred embodiment of the invention.

A second exemplary embodiment of the invention is shown in FIG. 2. The isomerization unit feed is sent via line 202 to isomerization zone 22. Two recycle streams from the isomerized product fractionation zone are also sent to the isomerization zone. A normal pentane rich recycle stream is conducted via line 220 to line 202 and a C6 rich recycle stream is conducted via line 222 to line 202. The isomerization unit feed is mixed together with the normal pentane rich recycle stream and the C6 rich recycle stream and the three combined streams (the combined isomerization zone feed) are conducted via line 204 to isomerization zone 22.

Isomerization zone 22 shown in FIG. 2 illustrates the isomerization equipment and processes used to efficiently isomerize the combined isomerization zone feed which is conducted via line 204 to the isomerization zone. The combined isomerization zone feed is isomerized in isomerization zone 22 in the presence of isomerization catalysts and hydrogen. Isomerization may take place in one or more isomerization reactors in series arrangement.

The effluent stream from the isomerization reactors which are removed from isomerization zone 22 are sent to stabilizer 108 via line 206 to remove butane and light gases. A stabilized isomerized product is removed from the second end of stabilizer 108 and sent to a fractionation system consisting of a dividing wall column and a non-divided column to separate high octane streams from low octane streams. Butane and light gases are removed from the first end of stabilizer 108 via line 210. The stabilized isomerized product is sent to dividing wall column 114 via line 212. The dividing wall column contains two parallel fractionation zones which are divided by vertical dividing wall 116.

The stabilized isomerized product is introduced at an intermediate point to the feed side, or first parallel fractionation zone, of the dividing wall column. The entirety of Fraction A as well as a portion of Fractions B and C are driven upwards in the first parallel fractionation zone and enter the upper undivided section of the column. In the upper undivided section of the column, Fraction A is driven upwards to the top of the column and the portions of Fractions B and C which were driven upwards in the first parallel fractionation zone drain down into the second parallel fractionation zone. Fraction A is removed via line 218 from the first end of the column as a high octane isomerate product stream.

The entirety of Fractions D and E as well as a portion of Fractions B and C drain down through the first parallel fractionation zone and enter the lower undivided section of the column. The portions of Fractions B and C which drained down through the first parallel fractionation zone are driven upward into the second parallel fractionation zone.

A separation between Fraction B and Fraction C takes place in the second parallel fractionation zone. The portions of Fractions B and C which were driven upwards in the first parallel fractionation zone drain down into the top of the second parallel fractionation zone and the portions of Fractions B and C which drained down through the first parallel fractionation zone are driven upward into the bottom of the second parallel fractionation zone. Since Fraction B boils at a lower temperature than Fraction C, Fraction B will concentrate in the upper part of the second parallel fractionation zone and Fraction C will concentrate in the lower part of the second parallel fractionation zone. Fraction B is removed from the second parallel fractionation zone via line 220 as a first side draw from the column and returned to the isomerization zone. Fraction C is removed from the second parallel fractionation zone via line 221 as a second side draw from the column as a high octane isomerate product stream. Fraction B is removed from the column at an elevation that is higher than the elevation at which Fraction C is removed from the column.

In the lower undivided section of the column, Fraction E drains down to the bottom of the column and Fraction D drains down to an intermediate point in the lower undivided section of the column. Fraction E is removed via line 224 from the second end of the column as a high octane isomerate product stream. Fraction D is removed via line 222 from an intermediate point in the lower undivided section of the column as a third side draw from the column and returned to the isomerization zone.

The composite high octane isomerate product from the overall isomerization process in the first exemplary embodiment is comprised from the sum of Fractions A, C, and E. Each of these three fractions are removed from the isomerized product fractionation zone and combined to form the composite isomerate product from the overall isomerization process.

In the second exemplary embodiment of the invention shown in FIG. 2, five streams are removed from the dividing wall column. In this embodiment, Fractions D and E are separated in the lower undivided section of the dividing wall column. It is also possible, however, to perform the separation of Fractions D and E in a second non-divided column by removing only four streams rather than five from the dividing wall column. In the scenario where Fractions D and E are separated in a second non-divided column, the entirety of Fractions D and E drain down to the bottom of the dividing wall column. The stream removed from the second end of the dividing wall column containing a mixture of Fractions D and E would be sent to a second non-divided column to separate Fractions D and E.

In some applications with requirements for large isomerization reactors, it may be advantageous to reduce the recycle of C5s from the isomerized product fractionation zone to the isomerization zone through the use of a Depentanizer in a feed fractionation zone to strip a portion of the C5s from the isomerization unit feed and transfer the stripped C5s to the dividing wall column in the isomerized product fractionation zone of the present invention for additional separation into high octane and low octane streams.

The Depentanizer that is used with this invention to strip C5s from the isomerization unit feed is used in a configuration that is identical to a configuration which makes use of a Deisopentanizer as used in currently known art. The isomerization unit feed is sent to the Depentanizer in a feed fractionation zone, where a C5 rich stream is removed from the first end of the Depentanizer and sent to the dividing wall column in the isomerized product fractionation zone. The C5 rich stream from the Depentanizer represents a second feed to the dividing wall column in the isomerized product fractionation zone. The balance of the isomerization unit feed is removed from the second end of the Depentanizer and sent to an isomerization zone, where the balance of the isomerization unit feed is combined with low octane recycle streams from the isomerized product fractionation zone and the combined isomerization zone feed is isomerized in the presence of isomerization catalysts and hydrogen. The isomerized product stream from the isomerization zone is sent to an isomerized product fractionation zone, where the isomerized product stream is stabilized and separated into high octane and low octane streams.

The purpose of the Depentanizer is to remove as much isopentane as possible from the isomerization unit feed with less energy usage than a conventional Deisopentanizer. In order to remove a large portion of isopentane from the isomerization unit feed without using as much energy as a conventional Deisopentanizer, the separation which takes place in the Depentanizer is generally less sharp than the separation which takes place in a conventional Deisopentanizer. A coarser separation can be achieved in the Depentanizer by permitting a significant amount of pentane to be included in the overhead distillate product stream which is sent to the dividing wall column in the isomerized product fractionation zone.

The primary advantage of providing a Depentanizer in these applications is that the majority of isopentane molecules present in the isomerization unit feed are removed in the Depentanizer and bypass the isomerization zone. Removing the majority of isopentane molecules from the isomerization unit feed will improve the conversion of normal pentane found in the combined isomerization zone feed, because the isomerization reactor equilibrium is shifted in the direction of less normal pentane in the reactor effluent. The increased conversion of normal pentane in the isomerization zone results in less recycle of normal pentane from the isomerized product fractionation zone to the isomerization zone. As a result, the isomerization reactor size (as well as installed cost) is reduced through the use of a Depentanizer with the present invention.

The function of a Depentanizer in applications with requirements for large isomerization reactors is similar to the function of a Deisopentanizer as used in current known art, but the Depentanizer is not required to produce an overhead distillate product of the same purity as a Deisopentanizer. A Deisopentanizer must produce a high purity isopentane overhead distillate product in order to achieve a high isomerate product RON because the overhead distillate product from the Deisopentanizer is sent directly to the isomerate product pool. A Depentanizer that is used in conjunction with the present invention, however, does not send the overhead distillate product directly to the isomerate product pool; instead the overhead distillate product from the Depentanizer is sent to the dividing wall column in the isomerized product fractionation zone for additional separation of high octane compounds and low octane compounds. The Depentanizer will require significantly lower energy input than a Deisopentanizer as used in current known art because a lower purity overhead distillate product can be specified for the Depentanizer.

The optimal inlet point on the dividing wall column where the Depentanizer overhead distillate product is sent will depend upon the composition of the Depentanizer overhead distillate product. In general, the preferred inlet points will be in the undivided section of the dividing wall column above the first and second parallel fractionation zones or in the first parallel fractionation zone of the dividing wall column at an elevation which is higher than the inlet point of the stabilized isomerized product.

The claimed invention is:

1. An isomerization process having an isomerized product fractionation zone, said process comprising:
   contacting a combined isomerization zone feed comprising at least normal pentane and normal hexane with an isomerization catalyst in an isomerization zone to isomerize at least a portion of the normal pentane and normal hexane and form an isomerization zone effluent comprising at least $C_5$-$C_6$ normal and branched paraffins;
   passing the isomerization zone effluent into an isomerized product fractionation zone comprising a stabilizer and a dividing wall column, wherein the isomerization zone effluent is passed into a stabilizer to remove butane and light gases and form a stabilized isomerized product;
   passing the stabilized isomerized product into a dividing wall column divided into at least a first and second parallel fractionation zones by a dividing wall, with the first and second fractionation zones each having an upper end and a lower end located within the dividing wall column, wherein the first and second parallel fractionation zones are in open communication at the upper ends with an undivided upper section of the column and wherein the first and second parallel fractionation zones are in open communication at the lower ends with an undivided lower section of the column, and wherein the stabilized isomerized product enters the column at an intermediate point in the first parallel fractionation zone; and
   removing at least three streams from the dividing wall column, wherein at least one side stream comprising normal pentane and paraffins containing 6 carbon atoms with at least two branches is removed from an intermediate point of the second parallel fractionation zone of the dividing wall column, and wherein a high octane stream comprising isopentane is removed from a first end of the dividing wall column.

2. The process according to claim 1, wherein said side stream is passed into a non-divided column.

3. The process according to claim 2, wherein a low octane stream comprising normal pentane is removed from a first end of the non-divided column; and wherein a high octane stream comprising paraffins containing 6 carbon atoms with at least two branches is removed from a second end of the non-divided column.

4. The process according to claim 1, wherein a high octane stream comprising hydrocarbons containing at least 7 carbon atoms is removed from a second end of the dividing wall column.

5. The process according to claim 1, wherein a low octane stream comprising normal hexane and paraffins containing 6 carbon atoms and a single branch is removed as a side stream from an intermediate point in the undivided lower section of the dividing wall column.

6. The process according to claim 1, further comprising passing an isomerization feed to a feed fractionation zone to separate a stream rich in molecules containing 5 carbon atoms comprising isopentane and passing said stream to the dividing wall column as a second feed to the dividing wall column, wherein said stream enters the dividing wall column at an intermediate point in the undivided upper section of the dividing wall column and wherein a remainder of the isomerization feed is passed to the isomerization zone as at least a part of the combined isomerization feed.

7. The process according to claim 1, further comprising passing an isomerization feed to a feed fractionation zone to separate a stream rich in molecules containing 5 carbon atoms comprising isopentane and passing said stream to the dividing wall column as a second feed to the dividing wall column, wherein said stream enters the dividing wall column at an intermediate point in the first parallel fractionation zone and wherein a remainder of the isomerization feed is passed to the isomerization zone as at least a part of the combined isomerization feed.

8. An isomerization process having an isomerized product fractionation zone, said process comprising:
   contacting a combined isomerization zone feed comprising at least normal pentane and normal hexane with an isomerization catalyst in an isomerization zone to isomerize at least a portion of the normal pentane and normal hexane and form an isomerization zone effluent comprising at least $C_5$-$C_6$ normal and branched paraffins;
   passing the isomerization zone effluent into an isomerized product fractionation zone comprising a stabilizer and a dividing wall column, wherein the isomerization zone effluent is passed into a stabilizer to remove butane and light gases and form a stabilized isomerized product;
   passing the stabilized isomerized product into a dividing wall column divided into at least a first and second parallel fractionation zones by a dividing wall, with the first and second fractionation zones each having an upper end and a lower end located within the dividing wall column, wherein the first and second parallel fractionation zones are in open communication at the upper ends with an undivided upper section of the column and wherein the first and second parallel fractionation zones are in open communication at the lower ends with an undivided lower section of the column, and wherein the stabilized isomerized product enters the column at an intermediate point in the first parallel fractionation zone; and
   removing at least four streams from the dividing wall column, wherein a low octane stream comprising normal pentane is removed as a first side stream from the second parallel fractionation zone of the dividing wall column and a high octane stream comprising paraffins containing 6 carbon atoms with at least two branches is removed as a second side stream from the second parallel fractionation zone of the dividing wall column, and wherein a high octane stream comprising isopentane is removed from a first end of the dividing wall column.

9. The process according to claim 8, wherein a high octane stream comprising hydrocarbons containing at least 7 carbon atoms is removed from a second end of the dividing wall column.

10. The process according to claim 8, wherein a low octane stream comprising normal hexane and paraffins containing 6 carbon atoms and a single branch is removed as a side stream from an intermediate point in the undivided lower section of the dividing wall column.

11. The process according to claim 8, further comprising passing an isomerization feed to a feed fractionation zone to separate a stream rich in molecules containing 5 carbon atoms comprising isopentane and passing said stream to the dividing wall column as a second feed to the dividing wall column, wherein said stream enters the dividing wall column at an intermediate point in the undivided upper section of the dividing wall column and wherein a remainder of the isomerization feed is passed to the isomerization zone as at least a part of the combined isomerization feed.

12. The process according to claim 8, further comprising passing an isomerization feed to a feed fractionation zone to separate a stream rich in molecules containing 5 carbon atoms comprising isopentane and passing said stream to the dividing wall column as a second feed to the dividing wall column, wherein said stream enters the dividing wall column at an intermediate point in the first parallel fractionation zone and wherein a remainder of the isomerization feed is passed to the isomerization zone as at least a part of the combined isomerization feed.

13. A process for separating an isomerization zone effluent in a product fractionation zone comprising a stabilizer and a dividing wall column, comprising:
   passing an isomerization zone effluent comprising at least C5-C6 normal and branched paraffins to a stabilizer to remove butane and light gases and form a stabilized isomerized product;
   passing the stabilized isomerized product into a dividing wall column divided into at least a first and second parallel fractionation zones by a dividing wall, with the first and second fractionation zones each having an upper end and a lower end located within the dividing wall column, wherein the first and second parallel fractionation zones are in open communication at the upper ends with an undivided upper section of the column and wherein the first and second parallel fractionation zones are in open communication at the lower ends with an undivided lower section of the column, and wherein the stabilized isomerized product enters the column at an intermediate point in the first parallel fractionation zone; and
   removing at least three streams from the dividing wall column, wherein at least one side stream comprising normal pentane and paraffins containing 6 carbon atoms with at least two branches is removed from an intermediate point of the second parallel fractionation zone of the dividing wall column, and wherein a high octane stream comprising isopentane is removed from a first end of the dividing wall column.

* * * * *